United States Patent
Faig et al.

(10) Patent No.: US 11,033,484 B2
(45) Date of Patent: Jun. 15, 2021

(54) SYNERGISTIC BLEND OF NATURAL OILS WITH APPLE CIDER VINEGAR FOR MAKE-UP REMOVAL

(71) Applicant: L'OREAL, Paris (FR)

(72) Inventors: Jonathan James Faig, Sayersville, NJ (US); David Chan, Edison, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/370,684

(22) Filed: Mar. 29, 2019

(65) Prior Publication Data

US 2020/0306170 A1    Oct. 1, 2020

(51) Int. Cl.
| | |
|---|---|
| *A61K 8/92* | (2006.01) |
| *A61K 8/362* | (2006.01) |
| *A61K 8/36* | (2006.01) |
| *A61K 8/73* | (2006.01) |
| *A61K 8/06* | (2006.01) |
| *A61K 8/04* | (2006.01) |
| *A61Q 1/14* | (2006.01) |

(52) U.S. Cl.
CPC ............... *A61K 8/922* (2013.01); *A61K 8/06* (2013.01); *A61K 8/361* (2013.01); *A61K 8/362* (2013.01); *A61K 8/737* (2013.01); *A61Q 1/14* (2013.01); *A61K 8/046* (2013.01); *A61K 2800/33* (2013.01); *A61K 2800/34* (2013.01); *A61K 2800/48* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 5,104,679 | A | * | 4/1992 | Jurcso ............... A23D 7/003 426/602 |
| 7,947,311 | B2 | | 5/2011 | Porter et al. |
| 9,700,507 | B1 | * | 7/2017 | Hakim ............... A61Q 19/007 |
| 2016/0120771 | A1 | * | 5/2016 | Simonet ............... A61K 8/58 132/206 |

FOREIGN PATENT DOCUMENTS

CN    107519066 A    12/2017

OTHER PUBLICATIONS

NaturalHairQueen ([https://naturalhairqueen.net/sweet-almond-oil-for-natural-hair/, published in 2017]) (Year: 2017).*
Hairfinity ([https://www.hairfinity.com/us/en/the-unexpected-benefits-of-olive-oil-for-hair/ 2015]). (Year: 2015).*

(Continued)

*Primary Examiner* — Kyung S Chang
(74) *Attorney, Agent, or Firm* — McNees Wallace & Nurick LLC

(57) ABSTRACT

A two-phase cosmetic composition includes an anhydrous phase and an aqueous phase in which the anhydrous and aqueous phases are separated by a single-phase interface. The anhydrous phase includes a plurality of fatty compounds and at least one thickener where the plurality of fatty compounds is present at about 30% by weight, based on the total weight of the composition, and the aqueous phase includes an acetic acid component.

11 Claims, 1 Drawing Sheet

(56) References Cited

OTHER PUBLICATIONS

Nutrition Action ([on-line website: http://1.bp.blogspot.com/-HAmvhnCLgHo/TIK7idEk-JI/AAAAAAAAA3g/YoTQFAToR-c/s1600/Picture+2.png, published in 2011]) (Year: 2011).*
Barclay-Nichols, "Apple Cider Vinegar in Cosmetics", Whoesale Supplied Plus. Retrieved from on-line website: [ https://www.wholesalesuppliesplus.com/handmade101/learn-to-make-articles/apple-cider-vinegar-in-Cosmetics.aspx] (Year: 2018).*
Fang et al., "Introduction to Environmental Geotechnology", see p. 36 section 2.8.1.,I 2016. (Year: 2016).*

* cited by examiner

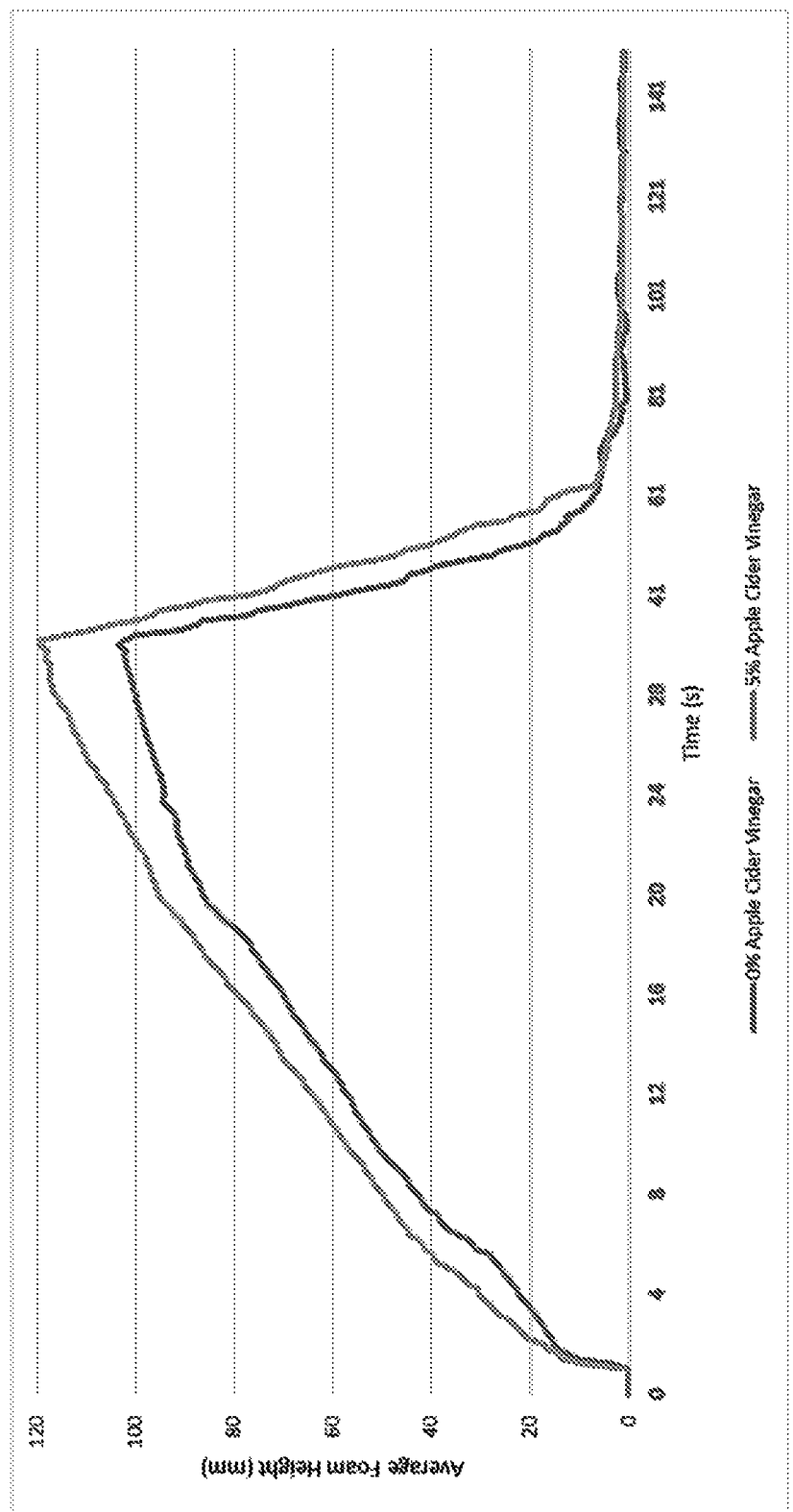

SYNERGISTIC BLEND OF NATURAL OILS WITH APPLE CIDER VINEGAR FOR MAKE-UP REMOVAL

FIELD OF THE INVENTION

The present invention relates to a composition for topical application comprising two separate phases, an aqueous phase and an anhydrous phase, which emulsify readily by shaking and which undergo rapid phase separation after the shaking is stopped. In particular, the present invention relates to the use of the two-phase composition in cosmetics or dermatology, and especially for removing make-up from, and for cleansing skin, particularly facial skin, and more particularly the eyes and lips. In some particular embodiments, the two-phase composition includes a blend of natural, plant-derived oils, natural gums, and apple cider vinegar to provide a make-up remover that performs as well as traditional, synthetic two-phase make-up remover formulations and micellar water formulations.

BACKGROUND OF THE INVENTION

For those who use facial make-up, particularly on a regular basis, there is the ongoing requirement of effectively removing existing make-up before applying new make-up, both to maintain good skin health and to facilitate the application of new make-up. Some cosmetic formulations that are specific for make-up removal include oil in water and water in oil emulsions including micellar cleansing waters, and bi-phase cleansers. Each of these types of products may include various synthetic and/or otherwise potentially irritating components that function to maintain emulsification of the phases in the case of emulsions or to maintain separation of the phases in the case of two-phase compositions. Emulsion based cleansers include at least two phases wherein at least one of the phases is dispersed in the other in the form of a multitude of droplets, and the interfaces are multiple and are generally stabilized with emulsifying surfactants and/or emulsifying polymers. These emulsifying components, particularly the surfactants, whether of natural or synthetic origin, may have the disadvantage of being irritating to the skin. In contrast to emulsions, bi-phase or two-phase compositions include two phases which are separated by a single-phase interface. Use of two-phase compositions necessitates prior shaking in order to form an extemporaneous emulsion wherein after shaking, the two phases become rapidly separated and regain their initial state. This phenomenon of rapid phase separation, or de-mixing, of the two phases after their use is one of the desired aesthetic qualities of two-phase compositions. In order to achieve distinct phase interface aspect of two-phase compositions, the products commonly include one or more synthetic components such as synthetic oils, for example, silicone oils, such as cyclopentasiloxane. Examples of such two-phase compositions in the art also include one or more surfactants. Consumers who seek cosmetic products that are less irritating, and that are formed on the basis of natural constituents, may seek to avoid cosmetics that include harsh ingredients such as emulsifying surfactants and polymers, and volatile silicone oils and other similar synthetic compositions. There is a need in the art for compositions, in particular two-phase make-up removing compositions that lack one or more of volatile silicone oils and surfactants while providing comparable or improved performance in one or more of removal of make-up and gentleness to skin and eyes.

The invention overcomes the disadvantages of the art as pertains to make-up removing compositions and provides a composition in an aesthetically pleasing two-phase formulation with a sharp phase interface and which allows easy make-up removal that is comparable to prior art compositions, and is not greasy, and includes little or no components that may be irritating to the skin or eyes.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

According to the disclosure, a two-phase make-up removing composition is provided, the composition comprising two or more fatty compounds and one or more thickeners in an upper anhydrous phase, wherein the two or more fatty compounds are in some embodiments selected from oils that comprise one or more fatty chain having a chain length from and including C8 to C24, and in some particular embodiments are selected from plant-derived oils. The composition further includes a lower aqueous phase that comprising an acetic acid component in a water-based solvent, and in some particular embodiments the acetic acid component is in the form of a vinegar, in some particular embodiments, apple cider vinegar. In some embodiments, the composition comprises in one or more of the anhydrous and aqueous phases one or more of hydrating agents, additional solvents, actives, vitamins, chelating agents. In some embodiments, the composition is essentially free of or is devoid of surfactant. In accordance with some embodiments, the composition is free or essentially free of one or more of synthetic oils and surfactants.

In accordance with some embodiments, the invention provides a two-phase cosmetic composition that includes an anhydrous phase and an aqueous phase in which the anhydrous and aqueous phases are separated by a single-phase interface. The anhydrous phase includes a plurality of fatty compounds and at least one thickener where the plurality of fatty compounds is present at about 30% by weight, based on the total weight of the composition, and the aqueous phase includes an acetic acid component. The composition may be characterized as surfactant free wherein the acetic acid component works synergistically with the fatty compounds to generate a foam in the composition upon agitation that is greater in foam height than is possible in the same composition that lacks the acetic acid component, whereby the acetic acid component has the effect of a surfactant.

In accordance with some particular embodiments, the invention provides a two-phase natural plant-derived cosmetic composition that includes an anhydrous phase and an aqueous phase. The anhydrous phase includes a blend of natural, plant-derived oils present in an amount that is at least about 30% by weight, based on the weight of the composition, and one or more natural gums present in the composition at a concentration, by weight, of from about 0.01% to about 0.5% by weight, based on the weight of the composition. The aqueous phase includes water and at least one plant-derived acetic acid component present in the composition at a concentration, by weight, of from about 0.5% to about 5%, based on the weight of the composition.

In accordance with some embodiments, the invention provides a two-phase cosmetic composition that includes in the anhydrous phase a plurality of fatty compounds that comprise oils that have different fatty acid compositions. In such embodiments, each of the oils comprises fatty acids that include monounsaturated fats in the range from about 60% to about 80%, and comprises saturated fatty acids present in the range from about 5% to about 15%, and comprises polyunsaturated fatty acids present in the range from about 10% to about 35%, all based on the total amount of fatty acid present in the oil.

In accordance with some particular embodiments, the invention provides a two-phase natural plant-derived cosmetic composition that includes an anhydrous phase and an aqueous phase. The anhydrous phase includes a blend of natural, plant-derived oils that include olive oil and sweet almond oil present in combination in an amount that is at least about 30% by weight, based on the weight of the composition, where the olive oil and sweet almond oil are present at a ratio of from about 1:1 to about 3:1. The anhydrous phase also includes one or more natural gums present in the composition at a concentration, by weight, of from about 0.01% to about 0.5% by weight, based on the weight of the composition. The aqueous phase includes water and apple cider vinegar present in the composition at a concentration, by weight, of from about 0.5% to about 5%, based on the weight of the composition.

Other features and advantages of the present invention will be apparent from the following more detailed description, by way of example, the principles of the invention.

This disclosure describes particular embodiments in accordance with the general inventive concepts and is not intended to limit the scope of the invention in any way. Indeed, the invention as described in the specification is broader than and unlimited by the particular embodiments set forth herein, and the terms used herein have their full ordinary meaning.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 1 is a graph showing foam height in formulations of the composition according to the disclosure.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

The term "keratinous tissue," as used herein, includes but is not limited to skin, hair, and nails.

The term "natural," as used herein refers to a compound or component that is obtained directly from the earth or soil or from plants or animals, via, if appropriate, one or more physical processes, such as grinding, refining, distillation, purification or filtration.

The term "food-derived," as used herein means extracted from a relevant part of a plant or animal or other source such as a bacterial culture.

The term "plant-derived," as used herein means extracted from a relevant part of a plant such as the seed, fruit or leaves, although equivalents which can be synthetically manufactured may be employed as well.

The term "plant-derived oils" as used herein means fatty plant-derived oils that contain one or more fatty chain, and in some embodiments the fatty chain has a chain length from and including C8 to C24. Thus, in some embodiments, a fatty plant-derived oil may comprise one or a blend of oils having a chain length of C8, C9, C10, C11, C12, C13, C14, C15, C16, C17, C18, C19, C20, C21, C22, C23, and C24.

The terms "free" and "devoid" indicates that no reliably measurable excluded material, for an excluded volatile silicone oil or excluded surfactant, is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" of a volatile silicone oil means that excluded material can be present in the composition at an amount of less than about 0.1% by weight, based on the total weight of the composition. Further, "essentially free" of a surfactant means that excluded material can be present in the composition at an amount of less than about 0.1% by weight, based on the total weight of the composition.

According to the disclosure, a two-phase make-up removing composition is provided, the composition comprising two or more fatty compounds and one or more thickeners in an upper anhydrous phase, wherein the two or more fatty compounds are in some embodiments selected from oils that comprise one or more fatty chain having a chain length from and including C8 to C24, and in some particular embodiments are selected from plant-derived oils. The composition further includes a lower aqueous phase that comprising an acetic acid component in a water-based solvent, and in some particular embodiments the acetic acid component is in the form of a vinegar, in some particular embodiments, apple cider vinegar. In some embodiments, the composition comprises in one or more of the anhydrous and aqueous phases one or more of hydrating agents, additional solvents, actives, vitamins, chelating agents. In some embodiments, the composition is essentially free of or is devoid of surfactant.

The composition provides the unexpected benefits of achieving efficient make-up removal that is comparable to other compositions that include one or more of volatile oils and/or surfactants and/or that lack naturally-derived components while being comparatively gentler, and in particularly being less irritating to the eyes and the skin surrounding the eyes of test users. The composition comprising apple cider vinegar also provides for a stable and sharp phase separation between the natural oil containing oil phase and the aqueous phase.

Anhydrous Phase

The anhydrous phase present in the cosmetic composition according to the disclosure includes at least two or more fatty compounds and at least one thickener. In accordance with the various embodiments, the amount of anhydrous phase present in the composition is in the range from about 25% to about 50%. The anhydrous phase is characterized as being free or essentially free of water and may be alternatively referred to as an oily phase.

Fatty Compounds

In accordance with the disclosure, a plurality of fatty compounds is present in the composition. In accordance with some embodiments, the plurality of fatty compounds includes two or more oils that comprise one or more fatty chain having a chain length from and including C8 to C24. In some embodiments, the oils are natural, food-derived oils, and in some particular embodiments, are oils of plant origin. Plant-derived oils include glyceride triesters, which are generally triesters of fatty acids and of glycerol, the fatty acids of which can have varied chain lengths from C4 to C24, it being possible for these chains to be saturated or unsaturated and linear or branched.

In accordance with the disclosure, in some embodiments, the plurality of fatty compounds comprises oils wherein at least two of the oils have fatty acid compositions that differ from one another. In such embodiments, each of the oils comprises fatty acids that include monounsaturated fatty acids present in the range from about 60% to about 80%, and comprises saturated fatty acids present in the range from about 5% to about 15%, and comprises polyunsaturated fatty acids present in the range from about 10% to about 35%, all based on the total amount of fatty acids present in the oil. In some such embodiments, one or more of the oils comprises fatty acids that include monounsaturated fatty acids in the range from about 70% to about 80%, and comprises saturated fatty acids present in the range from about 12% to about 15%, and comprises polyunsaturated fatty acids present in the range from about 10% to about 20%, and one or more of the oils comprises fatty acids that include monounsaturated fatty acids in the range from about 60% to about 68%, and comprises saturated fatty acids present in the range from about 5% to about 10%, and comprises polyunsaturated fatty acids present in the range from about 25% to about 35%, all based on the total amount of fatty acids in the oil. In a specific example, the oils comprise olive oil and sweet almond oil, the olive oil comprising about 75% monounsaturated, about 14% saturated, and about 11% polyunsaturated fatty acids, and the almond oil comprising about 62% monounsaturated, about 9% saturated, and about 29% polyunsaturated fatty acids, all based on the total amount of fatty acids present in the oil.

In some particular embodiments, the plurality of fatty compounds may be selected from olive oil, sweet almond oil, coconut oil, avocado oil, wheat germ oil, sunflower oil, grape seed oil, sesame oil, corn oil, apricot oil, castor oil, shea oil, soybean oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil. In some embodiments, the plurality of fatty compounds is selected from olive oil, sweet almond oil, coconut oil, avocado oil, and soybean oil. In a particular embodiment, the plurality of fatty compounds includes olive oil, sweet almond oil and soybean oil. In another embodiment, the plurality of fatty compounds includes olive oil and sweet almond oil.

In accordance with the various embodiments, each one of the plurality of fatty compounds is present in the composition at a concentration, by weight, of from about 1% to about 30%, or from about 3% to about 25%, or from about 5% to about 15%, or any suitable combination, sub-combination, range, or sub-range thereof by weight, based on the weight of the composition.

In accordance with the various embodiments, the plurality of fatty compounds as combined is present in the composition at a concentration, by weight, in an amount that is from about 15% to about 45%, or from about 25% to about 40%, or any suitable combination, sub-combination, range, or sub-range thereof by weight, based on the weight of the composition. And in some particular embodiments, the plurality of fatty compounds combined is present in an amount that is at least about 25%, or at least about 30% by weight, based on the weight of the composition. Thus, in some embodiments, the each one or combination of fatty compounds is present, by weight, based on the total weight of the composition, from about at least 1, 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 22, 34 35 36, 37, 38, 39, 40, 41, 42, 43, 44, 45 to about 45 weight percent, including increments and ranges therein and there between.

In accordance with some embodiments, the plurality of fatty compounds includes two oils which are present at a ratio, by weight, of from about 1:1 to about 3:1. In accordance with some such embodiments, the plurality of oils includes olive oil and sweet almond oil, wherein the combination is present in an amount that is at least about 30% by weight, based on the weight of the composition, and wherein the olive oil and sweet almond oil are present at a ratio of from about 1:1 to about 3:1. In accordance with such embodiments, olive oil is present in the composition in an amount from about 15% to about 27.5% by weight and sweet almond oil is present in an amount from about 2.5% to about 15% by weight, based on the weight of the composition. In some particular embodiments, the composition also includes another oil, for example soybean oil, which is present in an amount from about 0.005% to about 0.01% by weight, based on the weight of the composition.

Thickeners; Gums

In accordance with the disclosure, one or more thickeners is present in the composition. In some embodiments, the one or more thickeners is in the anhydrous phase. Thickeners can include one or more of cellulose-based thickeners (e.g., hydroxyethyl cellulose, hydroxypropyl cellulose, carboxymethylcellulose, cationic cellulose ether derivatives, quaternized cellulose derivatives, etc.), gums such as gums of microbial origin (e.g., xanthan gum, scleroglucan gum, etc.), and gums derived from plant exudates, including but not limited to guar gum and its derivatives (e.g., hydroxypropyl guar, cationic guar derivatives, etc.), gum arabic, ghatti gum, karaya gum, gum tragacanth, carrageenan gum, agar gum and carob gum, pectins, alginates, and starches. In some embodiments, the one or more thickeners is selected from gums. In some particular embodiments, the one or more thickeners is selected from polysaccharide gum, xanthan gum, locust bean gum and sclerotium gum. In a particular embodiment, the one or more thickeners includes xanthan gum.

In accordance with the various embodiments, the one or more thickeners is present in the composition at a concentration, by weight, of from about 0.01% to about 0.5% by weight, in some embodiments from about 0.01% to about 0.2% by weight, or from about 0.05% to about 0.09% by weight, or from about 0.05% to about 0.07% by weight based on the total weight of the composition. In some embodiments, the one or more thickeners is present from at least 0.01%, or from at least 0.05%, or from at least 0.5%. In some embodiments, the one or more thickeners is present up to but not more than about 0.5%, or not more than about 0.05%, not more than about 0.01%. Thus, each one of or the combination of one or more thickeners is present, by weight, based on the total weight of the composition, each one or the combination present from about 0.01, 0.02, 0.03, 0.04, 0.05, 0.06, 0.07, 0.08, 0.09, 0.1, 0.2, 0.3, 0.4 to about 0.5 weight percent, including increments and ranges therein and there between.

Aqueous Phase

The aqueous phase present in the cosmetic composition according to the disclosure includes water and an acetic acid component. In accordance with the various embodiments, the amount of aqueous phase present in the composition in in the range from about 50% to about 75%.

Acetic Acid Component

In accordance with the disclosure, the aqueous phase of the composition comprises one or more components comprising acetic acid. Nonlimiting examples of an acetic acid component include acetic acid, solvent diluted acetic acid; vinegar, including but not limited to apple cider vinegar, white wine vinegar, red wine vinegar, rice wine vinegar; and lemon juice. In some embodiments according to the disclosure, the aqueous phase of the composition comprises one or more forms of vinegar or vinegar extract. Vinegar is a sour liquid consisting of dilute and impure acetic acid, obtained by acetous fermentation from juice, wine, cider, beer, ale, or the like, and generally comprises about 5-20% acetic acid, water, and trace chemicals and extracts. In some particular embodiments, the acetic acid component is apple cider vinegar.

In accordance with the various embodiments, the amount of the one or more acetic acid component is present in the composition in the range from about 0.1% to about 20%, or from about 0.1% to about 15%, or from about 0.1% to about 10%, or from about 0.1% to about 5%, or any suitable combination, sub-combination, range, or sub-range thereof by weight, based on the weight of the composition. In some embodiments, the one or more acetic acid component is present from at least 0.1%, or from at least 0.5%, or from at least 1%. In some embodiments, the one or more acetic acid component is present up to but not more than about 10%, or not more than about 5%, not more than about 1%. Thus, any one or a combination of an acetic acid component may be present, by weight, based on the total weight of the composition, each one or the combination present from about 0.10, 0.20, 0.30, 0.40, 0.50, 0.60, 0.70, 0.80, 0.90, 1, 2, 3, 4, 5, 6, 7, 8, 9, 10, 11, 12, 13, 14, 15, 16, 17, 18, 19 to about 20 weight percent, including increments and ranges therein and there between.

Solvent

In accordance with the disclosure, the composition includes water in addition to one or more other solvents. In accordance with some embodiments, the composition includes one or more solvents comprising a glycol. Glycols may be selected from and include, by way of nonlimiting examples, propanediol, glycerin, caprylyl glycol, propylene glycol, polyethylene glycol, and other glycols, and combinations of these. In some particular embodiments, the solvents include water and propanediol.

In accordance with the various embodiments, the amount of water present in the composition ranges from about 50% to about 75%. In accordance with the various embodiments, the amount of the one or more additional solvents present in the composition ranges from about 1% to about 10%, or of from about 1% to about 5%, or from about 1% to about 3%, or any suitable combination, sub-combination, range, or sub-range thereof by weight, based on the weight of the composition. Thus, any one or a combination of solvents in addition to water may be present, by weight, based on the total weight of the composition, each one or the combination present from about 1, 2, 3, 4, 5, 6, 7, 8, 9 to about 10 weight percent, including increments and ranges therein and there between.

Actives/Additives

In accordance with the disclosure, in some embodiments, there may be one or more actives present in the cosmetic composition in one or both of the anhydrous and the aqueous phases. In some embodiments, actives used according to the disclosure may be selected from; anti-microbial components, including, but not limited to, capryloyl glycine and sodium salicylate; antioxidants, including, but not limited to, phenolic compounds, such as chalcones, flavones, flavanones, flavanols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, phenolic terpenes, resveratrol, curcumin, pinoresinol, ferulic acid, hydroxytyrosol, cinnamic acid, caffeic acid, p-coumaric acid, baicalin, pine bark extract, ellagic acid; and vitamins and vitamin derivatives, such as panthenol, tocopherol, ascorbic acid; conditioning agents such as the silicone oil dimethicone, allantoin and dicaprylyl carbonate; clays such as kaolin; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example Pyrus Malus (Apple) Fruit Extract, and Aloe Barbadensis Leaf Juice Powder; citric acid, sodium chloride; neutralizing or pH-adjusting agents (e.g., triethylamine (TEA) and sodium hydroxide); one or more hydrating agents selected from glycerin, squalane, sucrose, triacetin, monoethylene glycol, diethylene glycol, triethylene glycol, propylene glycol, butylene glycol, dipropylene glycol, diethylene glycol, hexylene glycol, glycol ethers such as monopropylene, dipropylene and tripropylene glycol alkyl(C1-C4)ethers, glycerol, xylitol, maltitol, sorbitol, pentaerythritol, inositol, pyrrolidone carboxylic acid, lactic acid, lithium chloride, acetamide MEA, sodium lactate, urea, dicyanamide, hyaluronic acid, aloe vera, honey, and seaweed extract; and combinations thereof. Although the optional active components are given as examples, it will be appreciated that other optional components compatible with cosmetic applications known in the art may be used.

Also, in accordance with the disclosure, in some embodiments, there may be one or more cosmetically acceptable additives present in the cosmetic composition. In some embodiments, cosmetically acceptable additives used according to the disclosure may be selected from colorants, preservatives, fragrances, dyes. Although the optional additives are given as examples, it will be appreciated that other optional components compatible with cosmetic applications known in the art may be used.

In some particular embodiments, the composition includes one or a combination of actives and additives selected from tocopherol, citric acid, sodium hydroxide, potassium sorbate, sodium benzoate and sodium chloride.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.05% to about 0.1%, or from about 0.15% to about 5%, or from about 0.40% to about 4%, or from about 0.5% to about 2% by weight, or from about 1% to about 2%, or any suitable combination, sub-combination, range, or sub-range thereof by weight, based on the weight of the composition. Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

The following examples are intended to further illustrate the present invention. They are not intended to limit the invention in any way. Unless otherwise indicated, all parts are by weight.

EXAMPLES

Raw Materials

Compositions as described herein according to the disclosure, and compositions as exemplified herein include raw materials selected from commercially available materials. In the examples, all raw materials are used at concentrations of 100% unless otherwise noted including, for example: Apple Cider Vinegar; Polysaccharide Gum; Xanthan Gum; Locust Bean Gum; Sclerotium Gum; Oil Blend (Sweet Almond Oil; Olive Oil); soybean oil.

Inventive Compositions

TABLE 1

Inventive Compositions (rinse off and leave on)

| Ingredient | Inventive 1 | Inventive 2 |
|---|---|---|
| Fruit Extract | 0.03 | 0.03 |
| Xanthan Gum/Thickener | 0.07 | 0.07 |
| Potassium Sorbate | 0.002 | 0.002 |
| Propanediol | 3 | 0 |
| Sodium Benzoate | 0.10 | 0.11 |
| Tocopherol | 0.05 | 0.05 |
| Sodium Chloride | 0.2 | 0.2 |
| Water | 66 | 69 |
| *Glycine Soja* (Soybean) Oil/Fatty Compound | 0.006 | 0.006 |
| *Olea Europaea* (Olive) Fruit Oil/Fatty Compound | 15 | 15 |
| *Prunus Amygdalus Dulcis* (Sweet Almond) Oil/Fatty Compound | 15 | 15 |
| Citric Acid | 0.03 | 0 |
| Vinegar/Acetic Acid Component | 0.9 | 0.9 |

Table 1 provides ingredients for two inventive embodiments of the composition according to the disclosure, including Inventive 1, which is a rinse off formulation, and Inventive 2, which is a leave on formulation of the composition according to the disclosure.

Comparative Compositions

TABLE 2A

Micellar Water Comparative

| Ingredient | Comparative 1: micellar water |
|---|---|
| Citric Acid | 0 |
| Sodium Hydroxide | 0 |
| Tocopherol | 0.004 |
| Propanediol | 2.3 |
| Pentylene Glycol | 3.8 |
| Decyl Glucoside/Surfactant | 0.06 |
| Glycerin | 7.5 |
| Dicaprylyl Ether | 13.9 |
| Salicylic Acid | 0.2 |
| Sea Salt | 1.2 |
| Water | 63.6 |
| Dipotassium Phosphate | 0.4 |
| Potassium Phosphate | 0.8 |
| Coco-Caprylate/Caprate | 6.1 |
| *Aloe Barbadensis* Leaf Juice Powder | 0.1 |

TABLE 2b

Bi-phase Comparative

| Ingredient | Comparative 2: bi-phase |
|---|---|
| Cyclopentasiloxane/silicone oil | 27.84 |
| Isohexadecane | 18.64 |
| Sodium Chloride | 0.48 |
| Poloxamer 184/surfactant | 0.267 |
| Hexylene Glycol | 0.267 |
| Dipotassium Phosphate | 0.16 |
| Benzyl Alcohol | 0.11 |
| Potassium Phosphate | 0.053 |
| Quaternium-15/surfactant | 0.027 |
| Benzalkonium Chloride/surfactant | 0.016 |
| Parfum/Fragrance | 0.001 |
| Citronellol | Trace |
| Geraniol | Trace |

Tables 2A and 2B provide ingredients for comparative compositions each of which lack the combination in the anhydrous phase of a plurality of fatty compounds and a thickener and lack in the aqueous phase an acetic acid component.

Testing

Performance Testing of Compositions with and Without Acetic Acid (Exemplified with Apple Cider Vinegar)

Referring now to the drawings, FIG. 1 provides a graph showing the performance of compositions according to the disclosure with and without the acetic acid component. The graph shows the results from foam height testing conducted on the aqueous phase of inventive compositions using a Kruss Dynamic Foam Analyzer (model DFA100). The compositions contained, respectively, 0% of acetic acid component and 5% of acetic acid component. As demonstrated by the results, the addition of the apple cider vinegar generates a greater foam height than composition lacking the apple cider vinegar, indicating the ability of the acetic acid component to act as a surfactant. And in combination with the anhydrous phase, the acetic acid component generating a synergistic effect to provide efficacy in the removal of cosmetic products, as shown in the following comparative tests.

Make-Up Removal Efficacy of Inventive Compositions

Several alternate combinations of fatty compound oil blends in the anhydrous phase of the inventive composition were assessed via a foundation removal study in which varying ratios of the different oils were screened with the other anhydrous phase and the aqueous phase components held constant. In the study 0.1 grams of foundation was applied evenly to forearms and allowed to dry. Then 3 mL of each bi-phase composition according to the disclosure was applied to a cotton pad and allowed to absorb. Make-up removal efficacy was assessed by the number of cotton pads needed to completely remove foundation when using ten swipes per pad.

Referring to the results shown in Table 3, the tests demonstrated that some combinations of oils, in particular olive oil and sweet almond oil provided in a ratio of from 1:1 to 3:1, provide enhanced efficacy of removal with the fewest cotton pads (2) as compared to other combinations of oils that required more pads (3 or 4).

Top performing systems were then screened with and without apple cider vinegar to confirm the increased efficacy in apple cider-containing bi-phases.

TABLE 3

Make-up Removal Efficacy of Inventive Compositions

| Inventive | Olive | Safflower | Coconut | Almond | Cotton Pads |
| --- | --- | --- | --- | --- | --- |
| 1 | 15 | 0 | 0 | 15 | 2 |
| B | 7.5 | 15 | 7.5 | 0 | 3 |
| C | 30 | 0 | 0 | 0 | 3 |
| D | 0 | 15 | 7.5 | 7.5 | 3 |
| E | 7.5 | 7.5 | 0 | 15 | 3 |
| F | 15 | 15 | 0 | 0 | 3 |
| G | 0 | 22.5 | 0 | 7.5 | 3 |
| H | 22.5 | 0 | 7.5 | 0 | 4 |
| I | 0 | 0 | 7.5 | 22.5 | 3 |
| J | 0 | 15 | 0 | 15 | 3 |
| K | 22.5 | 0 | 0 | 7.5 | 2 |
| L | 0 | 30 | 0 | 0 | 4 |
| M | 15 | 0 | 7.5 | 7.5 | 3 |
| N | 7.5 | 0 | 0 | 22.5 | 3 |
| O | 7.5 | 22.5 | 0 | 0 | 4 |
| P | 22.5 | 7.5 | 0 | 0 | 3 |
| Q | 0 | 0 | 0 | 30 | 3 |
| R | 0 | 15 | 15 | 0 | 3 |
| S | 7.5 | 0 | 15 | 7.5 | 3 |
| T | 7.5 | 15 | 0 | 7.5 | 3 |
| U | 15 | 7.5 | 0 | 7.5 | 3 |
| V | 27.5 | 0 | 0 | 2.5 | 2 |

User Qualitative Testing of Inventive and Comparative Compositions

Table 4 shows user qualitative test results with two comparatives and a rinse-off embodiment of the inventive composition. The data show that the inventive compositions are advantageous over the comparatives for their gentleness to the skin, and particularly the eyes, while providing comparable aesthetic/tactile properties.

TABLE 4

User Qualitative Testing (on a scale of 1-9).

| | TEST COMPOSITIONS | | |
| --- | --- | --- | --- |
| Qualitative Criteria | Comparative 1 | Comparative 2 | Inventive 1 |
| Product effectively removes all traces of eye make-up | 7.57 | 6.57 | 7.57 |
| Product does not leave greasy/oily feel on eyes | 7.43 | 7.71 | 5.57 |
| Product feels gentle on eyes | 7.14 | 5.71 | 8.14 |
| Overall, I am satisfied with this product's performance | 7.00 | 5.57 | 6.71 |
| Additional Comments | burned/irritated eyes; felt similar to Comparative 2 FLA #8241070106 | burned/irritated eyes; felt similar to Comparative 1 | most gentle on skin |

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more," as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A two-phase cosmetic composition, comprising:
   a skin cleanser comprising an anhydrous phase and an aqueous phase:
   a. the anhydrous phase comprising a plurality of fatty compounds and at least one thickener:
      the plurality of fatty compounds including olive oil and sweet almond oil present at a ratio of from about 1:1 to about 3:1;
      the plurality of fatty compounds as combined being present in the composition at 15% to 40%, by weight, of the total weight of the composition; and
      the at least one thickener being present in the composition at about 0.01% to about 0.5%, by weight, of the total weight of the composition; and
   b. the aqueous phase comprising at least one acetic acid component present in the composition at about 0.5% to about 5%, by weight, of the total weight of the composition,
   wherein the anhydrous phase and the aqueous phase are separated by a single-phase interface,
   wherein the anhydrous phase and the aqueous phase emulsify readily with one another upon shaking to form an extemporaneous emulsion that undergoes rapid phase separation after the shaking has ceased, and
   wherein the composition is characterized as surfactant free and wherein the at least one acetic acid component works synergistically with the plurality of fatty compounds to generate a foam in the composition upon agitation that is greater in foam height than is possible in an otherwise identical comparative composition that lacks the at least one acetic acid component, whereby the at least one acetic acid component has the effect of a surfactant.

2. The two-phase cosmetic composition of claim 1, wherein one or more of the at least one thickener, and the at least one acetic acid component is food-derived.

3. The two-phase cosmetic composition of claim 1, wherein the plurality of fatty compounds as combined is present in the composition at a concentration, by weight, in an amount that is at least about 30% and up to 40%.

4. The two-phase cosmetic composition of claim 1, wherein the olive oil is present in the composition in an amount from about 15% to about 27.5% by weight and the sweet almond oil is present in an amount from about 2.5% to about 15% by weight, based on the weight of the composition.

5. The two-phase cosmetic composition of claim 4, wherein each of the olive oil and the sweet almond oil comprises fatty acids that include monounsaturated fatty acids in the range from about 60% to about 80%, and comprises saturated fatty acids present in the range from about 5% to about 15%, and comprises polyunsaturated fatty acids present in the range from about 10% to about 35%, all based on the total amount of fatty acid %, all based on the total amount of fatty acids present in the oil.

6. The two-phase cosmetic composition of claim 4, wherein at least one of the olive oil and the sweet almond oil comprises fatty acids that include monounsaturated fatty acids in the range from about 70% to about 80%, and comprises saturated fatty acids present in the range from about 12% to about 15%, and comprises polyunsaturated fatty acids present in the range from about 10% to about 20%, and at least one of the olive oil and the sweet almond oil comprises fatty acids that include monounsaturated fatty acids in the range from about 60% to about 68%, and comprises saturated fatty acids present in the range from about 5% to about 10%, and comprises polyunsaturated fatty acids present in the range from about 25% to about 35%, all based on the total amount of fatty acids present in the olive oil and the sweet almond oil.

7. The two-phase cosmetic composition of claim 1, wherein the at least one thickener is selected from the group consisting of hydroxyethyl cellulose, hydroxypropyl cellulose, carboxymethylcellulose, cationic cellulose ether derivatives, quaternized cellulose derivatives, natural gums, gums of microbial origin, gums derived from plant exudates, pectins, alginates, starches, and combinations thereof.

8. The two-phase cosmetic composition of claim 6, wherein the at least one thickener is selected from the group consisting of polysaccharide gum, xanthan gum, locust bean gum, sclerotium gum, and combinations thereof.

9. The two-phase cosmetic composition of claim 1, wherein the acetic acid component in the aqueous phase is selected from the group consisting of acetic acid, plant-derived acetic acid, apple cider vinegar, white wine vinegar, red wine vinegar, rice wine vinegar, lemon juice, and combinations thereof.

10. The two-phase cosmetic composition of claim 1, wherein the composition comprises one or more additives selected from the group consisting of anti-microbial components, antioxidants, vitamins, vitamin derivatives, conditioning agents, clays, essential oils, citric acid, sodium chloride, neutralizing agents, hydrating agents, colorants, preservatives, fragrances, dyes, and combinations thereof.

11. A two-phase derived cosmetic composition, comprising:
   a skin cleanser comprising an anhydrous phase and an aqueous phase,
   a. the anhydrous phase comprising a blend of natural, plant-derived oils comprising olive oil and sweet almond oil present in combination in an amount that is at least about 30% by weight, based on the weight of the composition, wherein the olive oil and the sweet almond oil are present at a ratio of from about 1:1 to about 3:1, and one or more natural gums present in the composition at a concentration, by weight, of from about 0.01% to about 0.5% by weight, based on the weight of the composition; and
   b. the aqueous phase comprising water and apple cider vinegar present in the composition at a concentration, by weight, of from about 0.5% to about 5%, based on the weight of the composition,
   wherein the anhydrous phase and the aqueous phase are separated by a single-phase interface,
   wherein the composition is characterized as surfactant free and wherein the acetic acid component works synergistically with the fatty compounds to generate a foam in the composition upon agitation that is greater in foam height than is possible in an otherwise identical comparative composition that lacks the acetic acid component, whereby the acetic acid component has the effect of a surfactant, and
   wherein the anhydrous phase and the aqueous phase emulsify readily with one another upon shaking to form an extemporaneous emulsion that undergoes rapid phase separation after the shaking has ceased.

* * * * *